(12) United States Patent
Ward

(10) Patent No.: US 8,623,049 B2
(45) Date of Patent: Jan. 7, 2014

(54) SOFT TISSUE ANCHOR AND METHODS AND APPARATUS FOR SECURING SOFT TISSUE

(75) Inventor: Thomas J. Ward, Columbus, OH (US)

(73) Assignee: Tendon Technology, Ltd., Columbus, OH (US)

( * ) Notice: Subject to any disclaimer, the term of this patent is extended or adjusted under 35 U.S.C. 154(b) by 1081 days.

(21) Appl. No.: 11/862,854

(22) Filed: Sep. 27, 2007

(65) Prior Publication Data

US 2008/0082130 A1    Apr. 3, 2008

Related U.S. Application Data

(60) Provisional application No. 60/827,345, filed on Sep. 28, 2006.

(51) Int. Cl.
*A61B 17/04* (2006.01)
*A61B 17/58* (2006.01)

(52) U.S. Cl.
USPC .......................... 606/232; 606/104

(58) Field of Classification Search
USPC ........................................................ 606/232
See application file for complete search history.

(56) References Cited

U.S. PATENT DOCUMENTS

| | | | |
|---|---|---|---|
| 196,621 A | 10/1877 | Barion | |
| 471,734 A | 3/1892 | Maier, Jr. | |
| 4,595,007 A | 6/1986 | Mericle | |
| 4,762,453 A * | 8/1988 | DeCaro | 411/383 |
| 5,582,616 A | 12/1996 | Bolduc et al. | |
| 5,662,683 A | 9/1997 | Kay | |
| 5,728,116 A * | 3/1998 | Rosenman | 606/151 |
| 5,810,882 A | 9/1998 | Bolduc et al. | |
| 6,083,244 A | 7/2000 | Lubbers et al. | |
| 6,527,774 B2 * | 3/2003 | Lieberman | 606/301 |
| 6,544,272 B1 | 4/2003 | Jakob et al. | |
| 6,984,241 B2 | 1/2006 | Lubbers et al. | |
| 2002/0077631 A1 | 6/2002 | Lubbers et al. | |
| 2004/0033318 A1 | 2/2004 | Kijima et al. | |
| 2004/0193217 A1 | 9/2004 | Lubbers et al. | |

OTHER PUBLICATIONS

U.S. Patent and Trademark Office, International Search Report and Written Opinion in PCT Application No. PCT/US07/79878, Mar. 13, 2008.

* cited by examiner

*Primary Examiner* — Tuan V Nguyen
(74) *Attorney, Agent, or Firm* — Wood, Herron & Evans, L.L.P.

(57) ABSTRACT

An apparatus for anchoring in soft tissue generally includes an elongate tensile member adapted to extend within the interior of soft tissue and a first helical anchor configured for insertion within the interior of the soft tissue. The first helical anchor extends along a lengthwise axis of rotation and includes a proximal coil extending around the axis and a distal coil portion ending in a distal tip. The proximal coil defines an outer diameter adjacent to the distal coil portion, and the distal tip is positioned radially outward of the outer diameter. A drive member is coupled with the first helical anchor such that the drive member may be used to rotate the first helical anchor into the soft tissue.

7 Claims, 2 Drawing Sheets

SOFT TISSUE ANCHOR AND METHODS AND APPARATUS FOR SECURING SOFT TISSUE

This application claims the priority benefit of U.S. Provisional Application Ser. No. 60/827,345, filed on Sep. 28, 2006 (expired), the disclosure of which is hereby fully incorporated by reference herein. This application also generally relates to U.S. Pat. Nos. 6,083,244 and 6,984,241, and U.S. patent application Ser. Nos. 10/816,725, filed on Apr. 2, 2004 (now U.S. Pat. No. 7,611,521); Ser. No. 10/300,183, filed on Nov. 20, 2002 (abandoned); and Ser. No. 10/620,932, filed on Jul. 16, 2003 (now U.S. Pat. No. 7,708,759. The disclosures of the above-mentioned U.S. patent and U.S. patent applications are hereby fully incorporated by reference herein.

FIELD OF THE INVENTION

The present invention generally relates to soft tissue repair, including tendon or ligament repair apparatus and methods. More specifically, the invention relates to the repair of severed or otherwise damaged tendons or ligaments and the attachment of tendons or ligaments to bone. As used herein, the terms "tendon" and "ligament" are used in a generally interchangeable manner. The term "soft tissue" includes tendons and ligaments, as well as other soft tissue such as muscle tissue.

BACKGROUND

The repair of tendons or ligaments is a challenging and complication prone area of surgery. As one example, the dilemma in flexor tendon repair surgery in the hand is to adequately connect a severed tendon without compromising the functionality of the hand due to surgical intervention and repair techniques.

Tendons can sustain high tensile forces resulting from muscle contraction, yet are flexible enough to bend around bony surfaces and deflect beneath retinacula to change the final direction of muscle pull. Tendons attach muscle to bone and transmit tensile loads from muscle to bone thereby producing joint movement. Ligaments attach bone to bone and can flex to allow natural movement of the bones that they attach, but are strong and inextensible so as to offer suitable resistance to applied forces. Ligaments augment the mechanical stability of the joints. The biomechanical behavior of tendons and ligaments is viscoelastic or rate dependent, that is, their strength and stiffness increase with an increased loading rate. Bundles of collagen fibers embedded in a connecting matrix, known as ground substance, provide the load carrying elements of natural tendons and ligaments. The arrangement of the collagen fibers is nearly parallel in tendons, equipping them to withstand high unidirectional loads.

The less parallel arrangement of the collagen fibers in ligaments allows these structures to sustain predominant tensile stresses in one direction and smaller stresses in other directions. The ground substance in both tendons and ligaments acts generally as a cementing matrix holding the collagen fibers together. The ground substance retains large amounts of water essential to the non-compressive hydraulic function of the moving tissue. Also included in the tendon composition are elastic fibers, tenocytes, small blood vessels and nerves. In general, the cellular material (fibroblasts) occupies about 20% to 38% of the total tissue volume, while the ground substance matrix accounts for the remaining 62% to 80%. About 70% of the ground substance matrix consists of water absorbed in an open polysaccharide matrix.

Two types of tendons exist in the hand for connecting phalanx (finger) bones to the appropriate muscles. Flexor tendons, which are connected to the volar or palm side of the fingers, lend the ability to curl the fingers towards the palm. Extensor tendons, which are connected to the dorsal or backside of the fingers, return the curled fingers back into a straight position. Sheaths and retinacula restrain most tendons in the hand to some extent and keep them close to the skeletal plane so that they maintain a relatively constant moment arm rather than bowstringing across the joints. The pulley system of the flexor tendon sheath in the finger is the most highly developed of these restraints. The flexor tendon sheath pulley system permits the flexor tendons to maintain a relatively constant moment arm and helps minimize stress risers between tendon and sheath. This system serves three important functions. First, it allows smooth tendon gliding or lubrication; second, the retinacular reinforcing pulleys maintain the flexor tendons close to the surface of the finger bones, preventing bowstringing; and third, it provides an enclosed synovial fluid environment for tendon nutrition and lubrication. As the finger moves, each tendon slides a certain distance, which defines the "excursion of the tendon". Excursion takes place simultaneously in the flexor and extensor tendons during joint motion. The tendons of the agonist, or contracting muscle, displace in one direction. The tendons of the antagonist or resisting muscles displace in the opposite direction to accommodate the motion.

Today, the most common methods of repairing torn, severed or otherwise damaged tendons involve approximating the severed ends of the tendons and suturing one side of the tendon to the other thereby returning the tendon to its natural position. A popular suture technique is the so-called Kessler technique and slight modifications thereof. Some of the other techniques include the Becker, Savage, lateral trap, double loop locking suture, four-strand interlock and variations of the Halsted technique. Other methods place prosthetic material either within or around the tendon. Polyester strips and sleeves along with polyester mesh have been used to reinforce the suture/tendon interface to provide a stronger repair.

Since most suture-based tendon repairs reach their tensile limit at about 6 lbs., surgeons must balance the desire to have full and immediate active motion to prevent adhesions against the need for immobilization to prevent rupture of the repair. Earlier loading of a repaired tendon promotes a more rapid increase in repair strength. For a tendon to properly rejoin, the opposed tendon ends do not have to touch but they do need to be approximated within 1-2 mm of each other to properly reattach. Tendons will heal at a rate that is proportional to the load being applied during physical therapy.

Similar problems and issues are encountered when attaching tendons or ligaments to bone. That is, simply suturing the tendon or ligament to a bone anchor or using external tendon anchor members may not provide the necessary strength of repair. As further discussed above, these techniques also promote adhesion formation.

U.S. Pat. No. 6,984,241 discloses examples of generally helical type coil anchors used for soft tissue repair, such as tendon or ligament repair. This includes tendon-to-tendon repair, ligament-to-ligament repair, and tendon/ligament-to-bone repair, for example. Various systems are disclosed in the '241 patent including one or more anchors and one or more flexible tensile members, for example, to effect the repair of a tendon or ligament, including soft tissue-to-bone techniques. The use of a generally helical helical coil was found to allow the soft tissue fibers to be held within the coil under compression applied in a direction generally perpendicular to the long axes of the fibers. This firmly couples the coil to the soft tissue, such as the tendon or ligament. This then allowed significant tensile force to be applied to the tendon or ligament during the repair and rehabilitation processes. For example, a flexible tensile member such as a suture could then be used to pull the tendon or ligament to a desired repair position, such as toward an opposing severed tendon or ligament end, or toward a bone.

Despite the significant improvements set forth in the '241 patent, there remains a need for improvements that allow for even greater repair strength and smaller anchor sizes, for example. Anchor systems that allow for larger tensile loads to be applied at the repair site will, for example, allow the patient to have even more active physical therapy after surgery and faster, more successful recovery. Smaller anchor sizes that still provide superior repair strength would, for example, provide a less obtrusive anchor system at the repair site and give the surgeon greater flexibility in making the repair and the ability to more easily repair smaller tendons or ligaments.

SUMMARY

In an illustrative embodiment, an apparatus is provided for anchoring in soft tissue. The apparatus includes an elongate tensile member adapted to extend within the interior of the soft tissue. A first helical anchor is configured for insertion within the interior of the soft tissue. The first helical anchor extends along a lengthwise axis of rotation and includes a proximal coil extending around the axis and a distal coil portion ending in a distal tip. The proximal coil defines an outer diameter adjacent to the distal coil portion. The distal tip is positioned radially outward of said outer diameter. It has been found, for example, that this distal tip design causes more fibers to be packed into the coil interior as the coil is rotated into fibrous soft tissue. A drive member is coupled with the first helical anchor such that the drive member may be used to rotate said first helical anchor into the soft tissue.

In alternative aspects, the distal tip tapers to a generally sharpened point. The drive member may further comprise a retaining member coupled for sliding movement along the elongate tensile member. The drive member may include a hole and the elongate tensile member can be received through the hole. The retaining member may further be configured to be at least partially received within the first helical anchor for creating a space between the retaining member and the first helical anchor for holding the fibers between the retaining member and the first helical anchor. The proximal coil may define a first outer diameter having a first radius and the distal coil portion may extend along a curvilinear path having a second radius greater than the first radius. The proximal coil may further comprises a plurality of proximal coils together defining the first outer diameter, which may be a constant diameter along a length of the anchor defined by the plurality of proximal coils.

In another embodiment, a helical tissue anchor is provided and comprises a helical coil structure including a proximal coil and a distal coil portion ending in a distal tip. The proximal coil defines an outer diameter adjacent to the distal coil portion, and the distal tip is positioned radially outward of the outer diameter. Other features of the helical tissue anchor may include, as non-limiting examples, those described herein.

A method of securing a helical anchor in tissue is provided and may generally utilize one or more anchors and other structure as described herein or as otherwise desired to effect a tissue repair. Generally, the method can comprise rotating a helical anchor formed as generally described above into the tissue, gathering tissue with the radially displaced distal tip of the anchor, and directing the gathered tissue further into an interior coil space defined within a proximal coil of the anchor. The method may further comprise gripping the tissue between the proximal coil and a retaining member contained at least partially within the interior coil space. The method may further comprise coupling an elongate tensile member to the helical anchor, and placing the elongate tensile member under tension while repairing the soft tissue. The method may still further comprise sliding the helical anchor along the elongate tensile member, and fixing the helical anchor to a position along the elongate tensile member.

These and other features, objects and advantages of the invention will become more readily apparent to those of ordinary skill in the art upon review of the following detailed description, taken in conjunction with the accompanying drawings.

DETAILED DESCRIPTION OF ILLUSTRATIVE EMBODIMENTS

Figure 1:
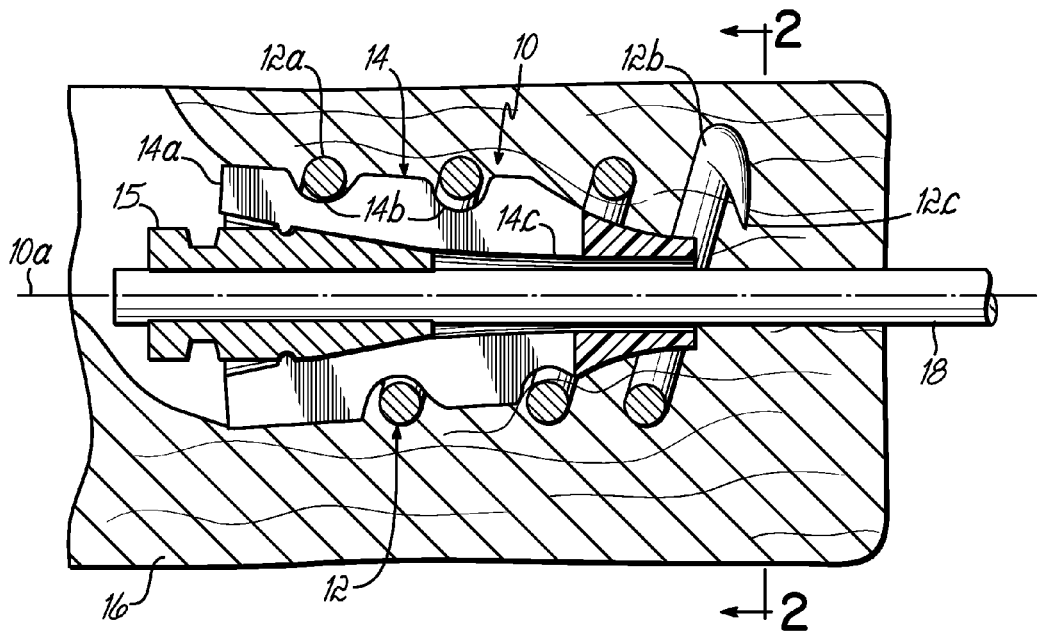
FIG. 1 is a cross sectional view of a first embodiment of an anchor assembly taken generally along the center longitudinal axis of the assembly and shown anchored within soft tissue and secured to an elongate tensile member.
Figure 1A:
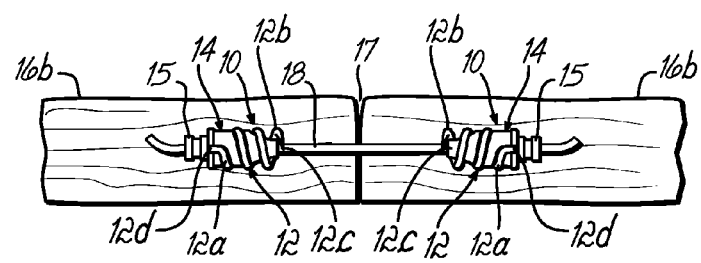
FIG. 1A is an elevational view showing two anchor assemblies and an elongate tensile member implanted within soft tissue, such as a tendon or ligament, to make a repair.
Figure 2:
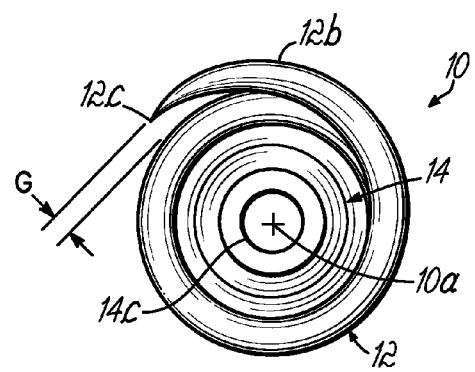
FIG. 2 is an end view taken generally along line 2-2 of FIG. 1.

FIGS. 1 and 2 illustrate an anchor assembly or structure 10 including a coil 12 having a proximal portion 12a, a distal portion 12b, and a distal, sharpened tip 12c. As illustrated, the proximal portion 12a may have a constant outer diameter, while the distal portion 12b has a larger radius of curvature than the radius of curvature associated with the outer diameter of the proximal portion 12a. A drive member in the form of an inner retaining member 14 may also be provided. The drive member may instead take other forms, and essentially serves to allow the assembly to be rotated about an axis 10a into tissue with a suitable tool (not shown) engaged with the proximal end 14a thereof. When used as a retaining member, soft tissue such as fibrous tissue 16 is trapped and compressed between the coil 12 and the retaining member 14 as will be described in connection with FIG. 2. FIG. 1A illustrates one possible repair assembly implanted in soft tissue segments 16a, 16b across a tear, cut, or injured portion 17 and generally comprised of two anchor assemblies 10 and an elongate tensile member 18. A locker element 15, such as a crimp, may be used to secure the anchor assembly 10 to a desired position along the elongate tensile member 18 after the assembly has been moved along the tensile member 18 during a surgical repair process. The locker element 15 may spread the retaining member apart radially as shown to assist with fiber retention, although this is not generally necessary.

Coil 12 and retaining member 14 may be constructed in a manner generally similar to or the same as the coils and retaining members as shown and described in the above-referenced '241 patent and related patent applications. As also shown in FIG. 1, the coil or anchor 12 may be retained in grooves 14b in the retaining member 14. FIG. 2 illustrates the coil 12 and retaining member 14, or anchor assembly 10, attached within soft tissue 16, which may be any soft tissue such as tendons, ligaments, muscles, etc. A central hole or bore 14c is provided in retaining member 14, for example, to slidably hold the elongate tensile member 18, which may be flexible and take the form of various types of suture, for example, depending on the needs of the surgical procedure. Although various designs are shown and described herein, many different coil designs and/or retaining member designs may be used instead, including any of the configurations illustrated in the above-referenced and incorporated patent and patent applications. Any of the other system components disclosed in the incorporated '241 patent and patent applications may also be used with assembly 10.

The improvement to which the present invention is generally directed involves the larger outer diameter associated with the distal coil portion 12b. For example, this distal coil portion 12b can provide a spacing or gap "G" of the distal tip 12c of the coil 12 outside of the outer diameter of the remaining more proximal portion 12a of the coil 12 as best shown in FIG. 1. As an example, when the proximal portion 12a has a constant outer diameter of 0.077", the gap G may be between about 0.005" and about 0.030". The coils may have a pitch of about 0.031" and the length of the coiled portion may be about 0.012". Of course, many different dimensions may be chosen depending on application needs.

The improved coil design has various advantages, including the ability to gather additional soft tissue fibers, such as tendon fibers, which greatly aids in preventing pullout of the anchor assembly or anchor structure 10 once installed into the soft tissue 16. In particular, as the coil 12 is rotated about the axis 10a into the tissue 16, the radially outwardly extending distal tip 12c will gather and pull in an additional amount of tissue fibers which will then be gathered and retained within the inner diameter of the coil 12, with or without the presence of the core or retaining member 14. The additional tissue fibers gathered as a result of the radially outwardly extending distal tip 12c, will become further compressed and held within the coil 12, such as between the inner diameter or surfaces of the coil 12 and the outer surface of the retaining member 14. The retention and compression of the soft tissue fibers between the inner surfaces of the coil 12 and the outer surface of the retaining member 14 leads to a high tensile strength connection between the anchor structure or assembly 10 and the soft tissue 16. Alternatively, a smaller anchor structure 10 may be used while achieving similar tensile strengths achieved by a larger anchor assembly or structure as shown in the above-incorporated '241 patent and patent applications. Thus, the anchor assembly 10 may be made smaller in various circumstances, such as for use in smaller tendons, ligaments or other soft tissue structures, or simply as a smaller, less obtrusive soft tissue anchor within a patient.

Although the components such as illustrated in FIGS. 1 and 2 may be utilized in many different types of surgical applications, a general repair technique may be described in connection with FIG. 1A. This technique, as well as other techniques, are more specifically described in the above incorporated patents and patent applications. In general, a method of securing the helical anchor 12 to soft tissue 16 may include rotating the helical anchor 12 into the soft tissue 16, gathering the soft tissue 16 with the distal tip 12c, and directing the gathered tissue 16 further into the interior coil space defined within the proximal coil or coils 12a. As more specifically set forth herein, the soft tissue 16 may be gripped between the proximal coil or coils 12a and a retaining member 14 contained at least partially within the interior coil space. For purposes of completing a repair that involves applying tension to the soft tissue 16, such as a pulling action on a tendon or ligament, the helical anchor 12 is coupled to the elongate tensile member 18. This may be accomplished by securing a crimp 15 against or into the proximal end 14a of the retaining member 14 as shown in FIG. 1. The elongate tensile member 18 may then be pulled to the right as viewed in FIG. 1 to place the elongate tensile member 18 and the attached soft tissue 16 under tension. For example, as shown in FIG. 1A, one severed or injured tendon or ligament segment 16a may be pulled toward or proximated with another segment 16b during the repair process. During this process, the helical anchor 12 may move along the elongate tensile member 18 such as by a sliding movement. More specific details on the various procedures that may be followed using the components described herein, as well as other components, may be found in the above incorporated '241 patent.

Figure 3:
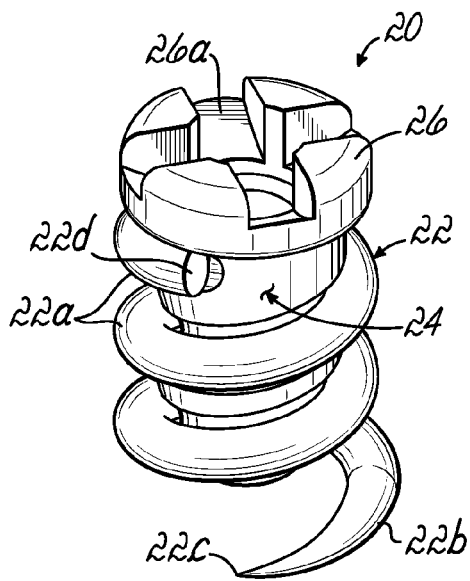
FIG. 3 is a perspective view of another illustrative embodiment of an anchor assembly.
Figure 4:
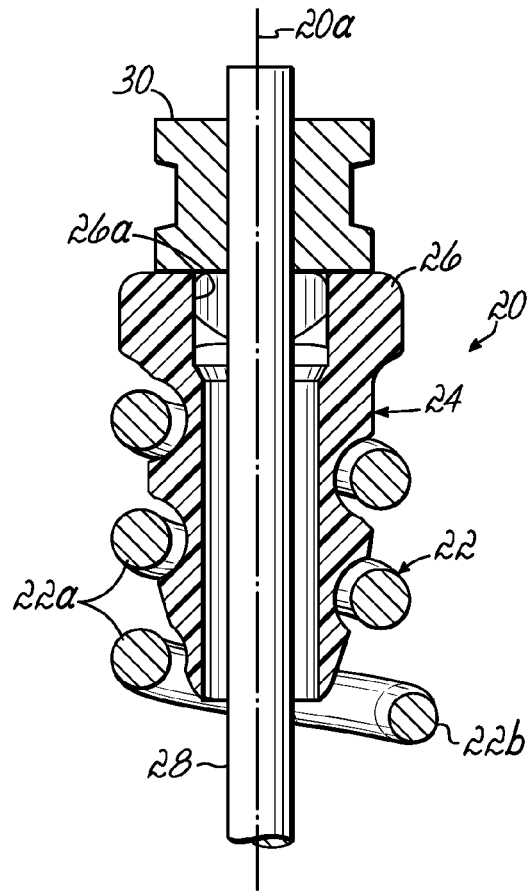
FIG. 4 is a cross sectional view taken generally along the center longitudinal axis of the anchor assembly shown in FIG. 3, and assembled with an elongate tensile member and locker element.
Figure 5:
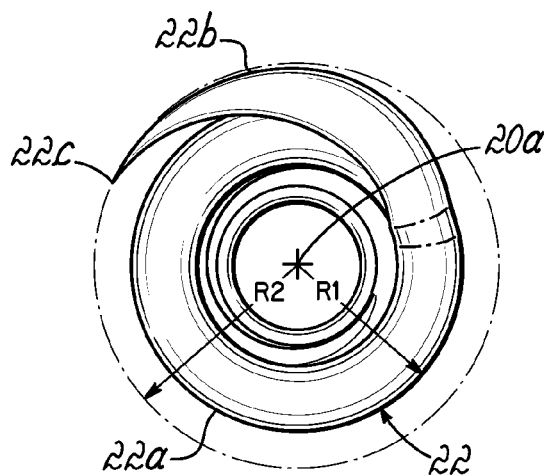
FIG. 5 is an end view of the generally helical coil shown in FIG. 3.

FIGS. 3-6 illustrate another illustrative embodiment. More specifically, FIG. 3 illustrates an anchor assembly 20 comprised of a generally helical coil type anchor 22 having a proximal portion 22a, a distal portion 22b and a sharp distal tip 22c, and a retaining member 24. The retaining member 24 is inserted into the interior of the coil 22 and includes a driver or head portion 26 with recesses 26a for accepting a tool (not shown). As previously described, a tool may be used for rotating the assembly 20 about axis 20a into soft tissue 16 as generally shown in FIGS. 1 and 1A, for example. FIG. 4 illustrates a cross sectional view of the anchor assembly 20 coupled to an elongate tensile member 28, such as a suture, and locked in place along the length of the suture 28 to prevent proximal movement of the anchor assembly 20 along the suture 28 after implantation. In this embodiment, a locker element 30 is shown as a crimp that does not enter the retaining member 24 but, rather, abuts the proximal end of the retaining member 24 as shown. The outer surface of the retaining member 24 has a rotary brushed A-FINE finish. The brushing or grinding action takes place in a circumferential direction around the outside surface of the retaining member 24 perpendicular to the long axis of the retaining member 24. The finish may be between a 6 micron and a 24 micron finish. This may be considered a circumferential finish grind on the outer surface of the retaining member 24. FIG. 5 illustrates that the distal portion 22b of the helical anchor or coil 22 including the sharpened tip or point 22c thereof, has been formed such as by bending outward to extend along a larger outer diameter than the immediately proximal portion 22a of the coil 22. In this regard, the radius R1 of the more proximal portion 22a of the coil 22 is less than the radius R2 of the distal portion 22b of the coil 22 including the distal tip 22c. For example, illustrative dimensions may be:

coil inner diameter: 0.047"
coil outer diameter: 0.077"
coil length: 0.099"
coil pitch: 0.031"
R1: 0.0235"
R2: 0.047"

Figure 6:
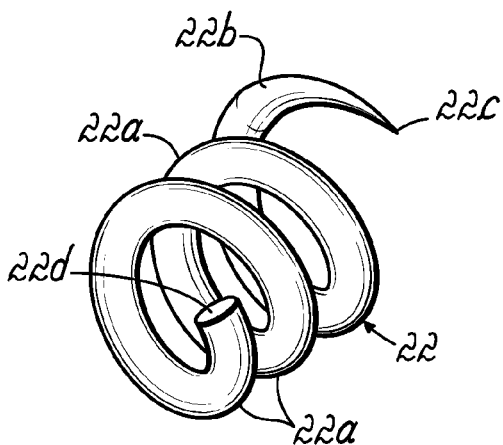
FIG. 6 is a perspective view of the generally helical coil of the assembly shown in FIG. 3.

FIG. 6 illustrates a perspective view of the coil 22. As appreciated from FIGS. 3 and 6, the proximal end 22d of the coil 22 generally follows the helix path of the coil 22 as opposed to being bent to follow along the long axis of the coil 22 as shown in FIG. 1A of the first embodiment. In either case, the coil 12, 22 may be rigidly fixed to the retaining member 14, 24 by a weld placed between the proximal end 12*d*, 22*d* of the coil or anchor 12, 22 and the corresponding location on the retaining member 14, 24. Each of these components may be formed from a suitable biocompatible material, such as a surgical grade stainless steel. The use and advantages of the embodiment shown in FIGS. 3-6 are as described above in connection with the first embodiment.

While the present invention has been illustrated by a description of various preferred embodiments and while these embodiments have been described in some detail, it is not the intention of the Applicant to restrict or in any way limit the scope of the appended claims to such detail. Additional advantages and modifications will readily appear to those skilled in the art. The various disclosed and incorporated features may be used alone or in any combination depending on the needs and preferences of the user. This has been a description of the present invention, along with the preferred methods of practicing the present invention as currently known. However, the invention itself should only be defined by the appended claims.

What is claimed is:

1. Apparatus for anchoring in soft tissue, the apparatus comprising:
    an elongate tensile member adapted to extend within the interior of the soft tissue;
    a first helical anchor configured for insertion within the interior of the soft tissue, said first helical anchor extending along a lengthwise axis of rotation and including a proximal coil extending around said axis and a distal coil portion ending in a distal tip, said proximal coil positioned immediately adjacent to said distal tip and defining an outer diameter immediately adjacent said distal coil portion and said distal tip, said proximal coil forming the next coil relative to the distal tip in a direction proximal to said distal tip, and said distal tip positioned radially outward of said outer diameter, wherein said proximal coil defines a first outer diameter having a first radius and said distal coil portion extends along a curvilinear path having a second radius greater than said first radius and wherein the curvilinear path extends less than one revolution; and
    a drive member coupled with said first helical anchor such that said drive member may be used to rotate said first helical anchor into the soft tissue.

2. The apparatus of claim 1, wherein said distal tip tapers to a generally sharpened point.

3. The apparatus of claim 1, wherein said drive member further comprises a retaining member coupled for sliding movement along said elongate tensile member.

4. The apparatus of claim 3, wherein said drive member includes a hole and said elongate tensile member is received through said hole.

5. The apparatus of claim 3, wherein said retaining member is configured to be at least partially received within said first helical anchor for creating a space between said retaining member and said first helical anchor for holding the fibers between said retaining member and said first helical anchor.

6. The apparatus of claim 1, wherein said proximal coil further comprises a plurality of proximal coils together defining said outer diameter.

7. The apparatus of claim 6, wherein said outer diameter is constant along a length of said first helical anchor defined by said plurality of proximal coils.

* * * * *